US009546342B1

(12) United States Patent
Sutterlin et al.

(10) Patent No.: US 9,546,342 B1
(45) Date of Patent: Jan. 17, 2017

(54) COMPLETE SAPONIFICATION AND ACIDULATION OF NATURAL OIL PROCESSING BYPRODUCTS

(71) Applicant: Inventure Renewables, Inc., Tuscaloosa, AL (US)

(72) Inventors: William Rusty Sutterlin, Hoov., AL (US); Nathan Killingsworth, Northport, AL (US); Cory Blanchard, Birmingham, AL (US); Ryan Long, Tuscaloosa, AL (US); Christopher Thomas Check, Tuscaloosa, AL (US)

(73) Assignee: Inveture Renewables, Inc., Tuscaloosa, AL (US)

( * ) Notice: Subject to any disclaimer, the term of this patent is extended or adjusted under 35 U.S.C. 154(b) by 0 days.

(21) Appl. No.: 15/293,274

(22) Filed: Oct. 13, 2016

Related U.S. Application Data

(63) Continuation of application No. PCT/US2016/023322, filed on Mar. 19, 2016.
(Continued)

(51) Int. Cl.
*C11B 13/02* (2006.01)
*C11C 1/02* (2006.01)
(Continued)

(52) U.S. Cl.
CPC ............ *C11B 13/02* (2013.01); *B01D 61/027* (2013.01); *B01D 61/147* (2013.01); *C07C 51/15* (2013.01);
(Continued)

(58) Field of Classification Search
CPC ............ C11B 3/04; C11B 3/06; C11B 13/02; C07C 51/15; C11C 1/025; C11C 1/08; C11C 3/003; B01D 61/027; B01D 61/147
See application file for complete search history.

(56) References Cited

U.S. PATENT DOCUMENTS

| 2,033,732 A | 3/1936 | Neiss |
| 2,812,343 A | 11/1957 | Cox et al. |
| 3,425,938 A | 2/1969 | Bloomberg et al. |

(Continued)

FOREIGN PATENT DOCUMENTS

| CN | 101565654 A | 10/2009 |
| CN | 103992883 | 8/2014 |

(Continued)

OTHER PUBLICATIONS

Akiya, Naoko, et al., "Roles of Water for Chemical Reactions in High-Temperature Water", Chem. Rev., vol. 102, (2002), pp. 2725-2750.
(Continued)

*Primary Examiner* — Yate K Cutliff
(74) *Attorney, Agent, or Firm* — Greer, Burns & Crain, Ltd.; Gregory P. Einhorn

(57) ABSTRACT

The present invention generally provides a process for treating a soapstock. The present invention more particularly provides systems and methods for treating a soapstock to generate free fatty acids and/or fatty acid derivatives, e.g. fatty acid alkyl esters. The present invention more particularly provides systems and methods for realizing the full fatty acid yield of a soapstock by first converting substantially all of the saponifiable material in a soapstock to salts of fatty acids (soaps) and acidulating the soaps to generate free fatty acids and/or fatty acid derivatives, e.g. fatty acid alkyl esters, wherein the soapstock comprises soaps and saponifiable lipids, e.g. glycerides and/or phospholipids, and the generating of free fatty acids and/or fatty acid is achieved without the use of a mineral acid.

12 Claims, 1 Drawing Sheet

Related U.S. Application Data

(60) Provisional application No. 62/245,468, filed on Oct. 23, 2015, provisional application No. 62/135,483, filed on Mar. 19, 2015.

(51) Int. Cl.

| | | |
|---|---|---|
| *C11C 3/00* | (2006.01) | |
| *C11C 1/08* | (2006.01) | |
| *B01D 61/02* | (2006.01) | |
| *B01D 61/14* | (2006.01) | |
| *C11B 3/06* | (2006.01) | |
| *C07C 51/15* | (2006.01) | |
| *C11B 3/04* | (2006.01) | |

(52) U.S. Cl.
 CPC .. *C11B 3/04* (2013.01); *C11B 3/06* (2013.01); *C11C 1/025* (2013.01); *C11C 1/08* (2013.01); *C11C 3/003* (2013.01)

(56) References Cited

U.S. PATENT DOCUMENTS

| | | |
|---|---|---|
| 3,428,660 A | 2/1969 | Morren |
| 3,901,869 A | 8/1975 | Bills |
| 4,075,188 A | 2/1978 | Vardell, Jr. |
| 4,100,181 A * | 7/1978 | Phillips ............... C11B 13/02 554/155 |
| 4,118,407 A | 10/1978 | Red et al. |
| 5,210,242 A | 5/1993 | Asbeck et al. |
| 5,283,319 A | 2/1994 | Huibers et al. |
| 5,286,845 A | 2/1994 | Huibers et al. |
| 5,487,817 A | 1/1996 | Fizet |
| 6,471,844 B1 | 10/2002 | Samuels |
| 6,475,758 B2 | 11/2002 | Reaney |
| 6,855,838 B2 | 2/2005 | Haas et al. |
| 7,705,170 B2 | 4/2010 | Geier et al. |
| 8,647,492 B2 | 2/2014 | Karanjikar et al. |
| 8,686,171 B2 | 4/2014 | McNeff et al. |
| 2005/0255174 A1 | 11/2005 | Shelley et al. |
| 2014/0135515 A1 | 5/2014 | Dasari et al. |
| 2016/0201010 A1 | 7/2016 | Berry et al. |

FOREIGN PATENT DOCUMENTS

| | | | |
|---|---|---|---|
| EP | 0 160 326 A1 | 12/1984 | |
| EP | 0406945 A2 | 1/1991 | |
| WO | 9323132 A2 | 11/1993 | |
| WO | 2005095565 A2 | 10/2005 | |
| WO | 2009017957 A1 | 2/2009 | |
| WO | 2015031857 A2 | 3/2015 | |
| WO | WO 2015/031857 | * | 3/2015 |
| WO | 2016100944 A2 | 6/2016 | |

OTHER PUBLICATIONS

Beal, R.E., et al., "Treatment of Soybean Oil Soapstock to Reduce Pollution", Journal of the American Oil Chemists' Society, vol. 49, May 19, 1972, pp. 447-450.

Dayton, Christopher Lore Gene, et al., "Enzymatic Degumming", Green Vegetable Oil Processing (2014), pp. 107-146.

Deng, Qi, et al., "Study on Saponification Technology of Waste Edible Oil", 2009 3rd International Conference on Bioinformatics and Biomedical Engineering, (2009), 4 pages.

Dowd, Michael, K., "Gas chromatographic characterization of soapstocks from vegetable oil refining", Journal of Chromatography A, vol. 816, (1998), pp. 185-193.

Dumont, Marie-Josée, et al., "Characterization of soapstock and deodorizer distillates of vegetable oils using gas chromatography", Lipid Technology, vol. 20, No. 6, (Jun. 2008), pp. 136-138.

Dumont, Marie-Josée, et al., "Soapstock and deodorizer distillates from North American vegetable oils: Review on their characterization, extraction and utilization", Food Research International, vol. 40, (2007), pp. 957-974.

Echim, Camelia, et al., "Production of biodiesel from side-stream refining products", Energy Environ. Sci., vol., 2, (2009), pp. 1131-1141.

Haas, Michael, J., et al., "Simple, High-Efficiency Synthesis of Fatty Acid Methyl Esters from Soapstock", JAOCS, vol. 77, No. 4, (2000), pp. 373-379.

Haas, Michael, J., et al., "Engine Performance of Biodiesel Fuel Prepared from Soybean Soapstock: A High Quality Renewable Fuel Produced from a Waste Feedstock", Energy & Fuels, vol. 15, (2001), pp. 1207-1212.

Haas, Michael, J., Improving the economics of biodiesel production through the use of low value lipids as feedstocks: vegetable oil soapstock, Fuel Processing Technology, vol. 86, (2005), pp. 1087-1096.

Hangx, S.J.T., "Subsurface Mineralisation: Rate of CO2 Mineralisation and Geomechanical Effects on Host and Seal Formations, Behaviour of the CO2-H2O system and preliminary mineralisation model and experiments" Tech. Utrecht University: HPT Laboratory, Department of Earth Sciences, CATO—CO2 capture, transport and storage towards a clean use of fossil fuels in the energy economy, CATO Workpackage WP 4.1, (Dec. 2005), 43 pages.

Jin, B., et al., "Comprehensive utilization of the mixture of oil sediments and soapstocks for producing FAME and phosphatides", Fuel Processing Technology, vol. 89, (2008), pp. 77-82.

Kulkarni, B.M., et al., "Investigation of Acid Oil as a Source of Biodiesel", Indian Journal of Chemical Technology, vol. 15, (Sep. 2008), pp. 467-471.

Santos, Regiane Ribeiro Dos, "Characterization of Different Oil Soapstocks and Their Application in the Lipase Production by Aspergillus niger under Solid State Fermentation" Journal of Food and Nutrition Research, vol. 2, No. 9, (2014), pp. 561-566.

Solvay, BicarZ, "Sodium Bicarbonate" Downloaded on Apr. 15, 2015, 3 pages.

United States Department of Agriculture, "Tall Oil Technical Evaluation Report", Jan. 31, 2010, 13 pages.

Watanabe, Yomi, et al., "Enzymatic Production of Fatty Acid Methyl Esters by Hydrolysis of Acid Oil Followed by Esterification", J Am Oil Chem Soc, vol. 84, (2007), pp. 1015-1021.

Woerfel, J.B., et al., "Processing and Utilization of By-Products from Soy Oil Processing", JAOCS, vol. 58, Issue 3, (Mar. 1981), pp. 188-191.

Woerfel, J.B., et al. "Alternatives for Processing of Soapstock", JAOCS, vol. 60, No. 2, (Feb. 1983), pp. 262A-265A.

Copenheaver, Blaine, R., "Written Opinion of the International Searching Authority", Patent Cooperation Treaty Application No. PCT/US2016/023322, International Searching Authority/United States, May 31, 2016, 4 pages.

Copenheaver, Blaine, R., "International Search Report of the International Searching Authority", Patent Cooperation Treaty Application No. PCT/US2016/023322, International Searching Authority/United States, May 31, 2016, 2 pages.

* cited by examiner

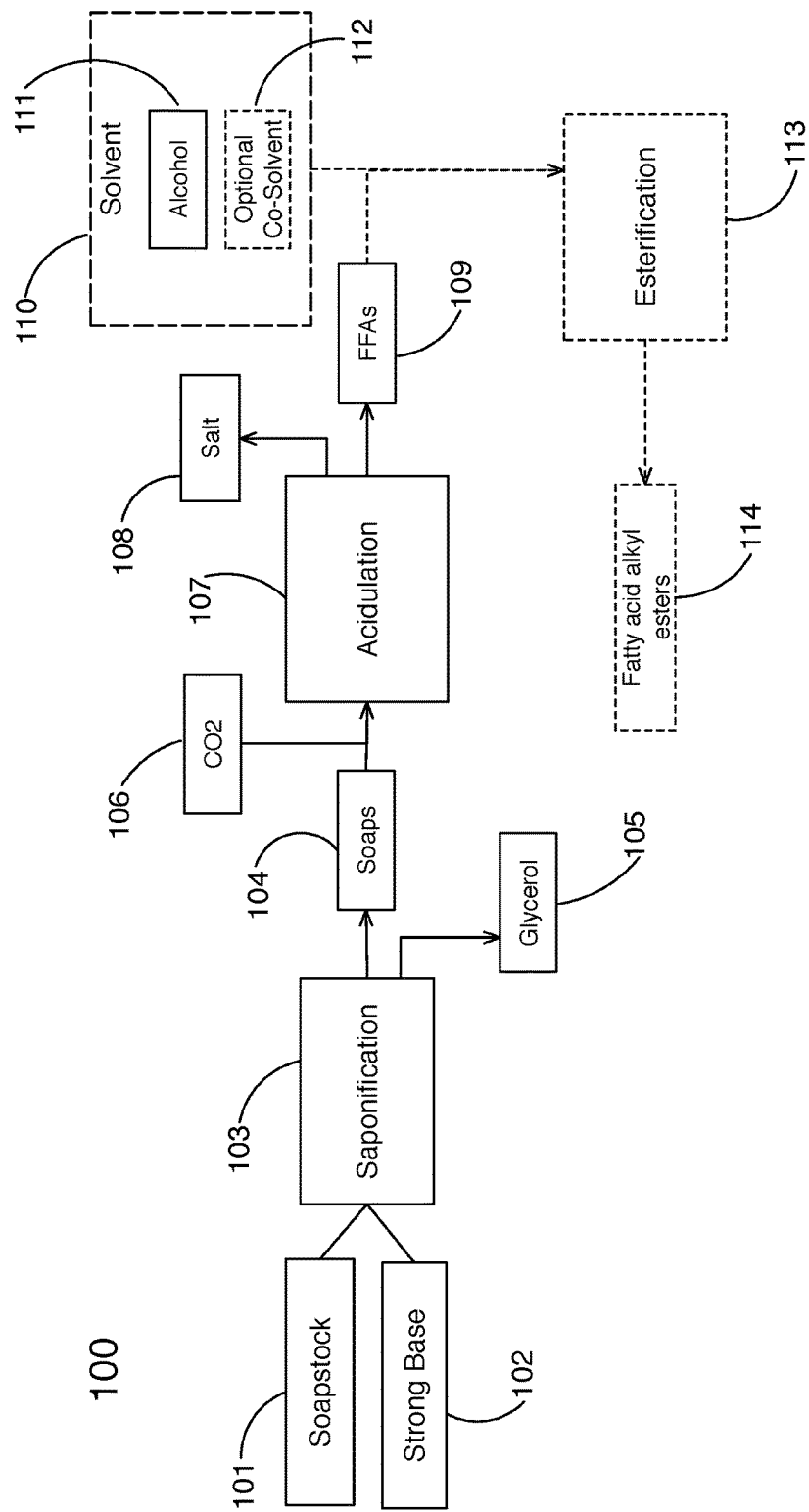

COMPLETE SAPONIFICATION AND ACIDULATION OF NATURAL OIL PROCESSING BYPRODUCTS

PRIORITY CLAIM

This application is a continuation application claiming benefit of priority under 35 U.S.C. §120 to Patent Convention Treaty (PCT) International Application Serial No. PCT/US2016/023322, filed Mar. 19, 2016, which claims the benefit of priority under 35 U.S.C. §119(e) of U.S. Provisional Application Ser. No. 62/245,468, filed Oct. 23, 2015; and U.S. Ser. No. 62/135,483, filed Mar. 19, 2015. The aforementioned applications are expressly incorporated herein by reference in their entirety and for all purposes.

FIELD OF THE INVENTION

The present invention generally provides a process for treating a soapstock. The present invention more particularly provides systems and methods for treating a soapstock to generate free fatty acids and/or fatty acid derivatives, e.g. fatty acid alkyl esters. The present invention more particularly provides systems and methods for realizing the full fatty acid yield of a soapstock by first converting substantially all of the saponifiable material in a soapstock to salts of fatty acids (soaps) and acidulating the soaps to generate free fatty acids and/or fatty acid derivatives, e.g. fatty acid alkyl esters, wherein the soapstock comprises soaps, saponifiable lipids, e.g. glycerides and/or phospholipids, and the generating of free fatty acids and/or fatty acid is achieved without the use of a mineral acid.

BACKGROUND OF THE INVENTION

Crude (unrefined) Animal and vegetable oils (referred to herein collectively as "natural oils") are typically subjected to a variety of processing steps to remove specific undesirable components of the crude oil prior to sale. The type, number, and sequencing of processing steps can vary depending on the crude oil feedstock, refinery type (e.g. physical vs. alkaline) and configuration, target product markets, and the like. In general, crude natural oils are refined to remove excess quantities of "gums" (comprised primarily of phospholipids), free fatty acids, as well as various coloring components and volatile compounds.

Once removed from the crude oil, the refining byproducts are either sold directly into low-value markets such as animal feed, or further processed into higher-value products. Two major byproducts of the chemical refining processes of natural oils are soapstock and gums.

In most natural oil refineries utilizing the chemical refining process, phosphoric acid or an equivalent acid is added to the crude oil to increase the solubility of the phospholipids (gums) in water. Next, a strong base, typically sodium hydroxide (NaOH) is added, reacting with the free fatty acids in the oil to form soaps (salts of free fatty acids). Water is then added to the oil to remove the soaps and solubilized gums. Soapstock is typically acidulated to generate free fatty acids. Gums are typically sold into low-value animal feed markets or upgraded to food-grade emulsifiers, e.g. lecithin.

In most chemical refining configurations, additional waste streams are generated which represent low- or negative-value byproducts. For example, it typically necessary to perform an additional water wash on the oil after the majority of the gums and soaps have been removed. The lipid content of this washwater (referred to as Soapstock Makeup) can contain from about 5% to about 20% soaps and other lipids, but the lipid content is generally not sufficiently high to justify the costs of further processing into value added products. In addition, all of the above referenced byproduct streams from the chemical refining process contain various amounts of saponifiable material that are not converted to free fatty acids.

Nothing in the prior art provides the benefits attendant with the present invention. Therefore, it is an object of the present invention to provide an improvement which overcomes the inadequacies of the prior art methods and devices and which is a significant contribution to the advancement to realizing the full fatty acid yield of saponifiable material.

Another object of the present invention is to provide a method for generating free fatty acids from a mixed lipid feedstock, the method comprising: providing the mixed lipid feedstock; combining the mixed lipid feedstock with a base to form a mixture; allowing the mixture to react in a reaction vessel; introducing carbon dioxide into the reacted mixture in the reaction vessel to form a first carbonic acid within the reaction vessel; mixing the first carbonic acid and the reacted mixture within the reaction vessel; allowing the first carbonic acid and reacted mixture to settle within the reaction vessel; and draining a first aqueous layer from the reaction vessel.

Yet another object of the present invention is to provide a method for generating free fatty acids from a mixed lipid feedstock, the method comprising: providing the mixed lipid feedstock; combining the mixed lipid feedstock with a base to form a mixture; allowing the mixture to react in a reaction vessel; introducing carbon dioxide into the reacted mixture in the reaction vessel to form a first carbonic acid within the reaction vessel; mixing the first carbonic acid and the reacted mixture within the reaction vessel; allowing the first carbonic acid and reacted mixture to settle within the reaction vessel; draining a first aqueous layer from the reaction vessel; collecting the first aqueous layer; and treating the collected first aqueous layer with calcium oxides, magnesium oxides, barium oxides, or other polyvalent oxides.

Still yet another object of the present invention is to provide a method for generating free fatty acids from a mixed lipid feedstock, the method comprising: providing the mixed lipid feedstock; combining the mixed lipid feedstock with a base to form a first mixture; allowing the first mixture to react in a reaction vessel; combining the reacted first mixture with an organic or inorganic acid, thereby acidulating soaps in the first mixture to generate free fatty acids; draining a first aqueous layer from the reaction vessel; combining the generated free fatty acids with an alcohol to form a second mixture; and heating and pressurizing the second mixture to above the critical temperature and pressure of the alcohol, thereby esterifying substantially all of the free fatty acids to generate fatty acid alkyl esters.

Another object of the present invention is to provide a method for generating free fatty acids from a mixed lipid feedstock, the method comprising: a) providing the mixed lipid feedstock; b) combining the mixed lipid feedstock with a base to form a first mixture; c) allowing the first mixture to react in a reaction vessel; d) introducing carbon dioxide into the reacted mixture in the reaction vessel to form a first carbonic acid within the reaction vessel; e) mixing the first carbonic acid and the reacted mixture within the reaction vessel; f) allowing the first carbonic acid and reacted mixture to settle within the reaction vessel; g) draining a first aqueous layer from the reaction vessel; h) removing a generated lipid layer from the reaction vessel; and i) repeating steps a) through h) above up to 8 times using the generated lipid layer from the reaction vessel as the mixed lipid feedstock for step a).

Yet another object of the present invention is to provide a method for generating an animal feed additive from a mixed lipid feedstock, the method comprising: providing the mixed lipid feedstock; combining the mixed lipid feedstock with a base to form a mixture; allowing the mixture to react in a reaction vessel; introducing carbon dioxide into the reacted mixture in the reaction vessel to form a first carbonic acid within the reaction vessel; mixing the first carbonic acid and the reacted mixture within the reaction vessel; allowing the first carbonic acid and reacted mixture to settle within the reaction vessel; draining a first aqueous layer from the reaction vessel; and concentrating the first aqueous layer to generate a sodium bicarbonate product that is substantially free of any water.

The foregoing has outlined some of the pertinent objects of the present invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The present invention provides a process for treating a soapstock. The present invention more particularly provides systems and methods for treating a soapstock to generate free fatty acids and/or fatty acid derivatives, e.g. fatty acid alkyl esters. The present invention more particularly provides systems and methods for realizing the full fatty acid yield of a soapstock by first converting substantially all of the saponifiable material in a soapstock to salts of fatty acids (soaps) and acidulating the soaps to generate free fatty acids and/or fatty acid derivatives, e.g. fatty acid alkyl esters, wherein the soapstock comprises soaps and saponifiable lipids, e.g. glycerides and/or phospholipids, and the generating of free fatty acids and/or fatty acid is achieved without the use of a mineral acid.

A feature of the present invention is to provide a method for generating free fatty acids from a mixed lipid feedstock. The method comprising the following steps as described herein. The mixed lipid feedstock is provided. The mixed lipid feedstock is combined with a base to form a first mixture. The first mixture is allowed to react. Carbon dioxide is introduced into the reacted mixture in the reaction vessel to form a first carbonic acid within the reaction vessel. The first carbonic acid is mixed with the reacted mixture within the reaction vessel. The first carbonic acid and reacted mixture are allowed to settle within the reaction vessel. A first aqueous layer is drained from the reaction vessel, thereby acidulating soaps in the first mixture to generate free fatty acids. The method can further comprise the following steps as described herein. The first aqueous layer can be filtered using a size exclusion filtration system. The filtering step can further comprise a filter having a membrane having a plurality of pores wherein the pores allow soaps and phosphates to pass through the membrane of the filter. The filtering step can further comprise a filter having a membrane wherein the membrane allows particles having a molecular weight less than the molecular weight of a salt to pass through the filter. The filtering step can further comprise maintaining a pH of the first aqueous layer between about 6 and 11. The filtering step can further comprise maintaining a pressure of the first aqueous layer between about 50 and 800 psi. The filtering step can further comprise maintaining a temperature of the first aqueous layer between about 23 and 100° C. The method can further comprise an electrolysis step wherein a lipid phase comprising a small amount of unreacted soaps is transferred to an electrolysis unit wherein the unreacted soaps in the lipid phase are reacted with an anolyte to generate free fatty acids. The method can further comprise concentrating the first aqueous layer from each step. The concentration step can further comprise maintaining a pH of the first aqueous layer between about 6 and 11. The concentration step can further comprise maintaining a pressure of the first aqueous layer between about 0 and 800 psi. The concentration step can further comprise maintaining a temperature of the first aqueous layer between about 23 and 100° C. The method can further comprise combining generated free fatty acids with an alcohol to form a second mixture; and heating and pressurizing the second mixture to above the critical temperature and pressure of the alcohol, thereby esterifying substantially all of the free fatty acids to generate fatty acid alkyl esters. The method can further comprise combining generated free fatty acids with an alcohol to form a second mixture; and reacting the second mixture to form a fatty alkyl ester. The method can further comprise using a catalyst to cause the reaction of the mixed lipid feedstock with the base. The catalyst can be an acid catalyst. The method can further comprise removing generated free fatty acids from neutral lipids; and reacting the neutral lipids to form a fatty alkyl ester. The method can further comprise using a catalyst to cause the reaction of the neutral lipids. The catalyst can be a base catalyst. The method can further comprise an electrolysis step wherein a lipid phase comprising a small amount of unreacted soaps is transferred to an electrolysis unit wherein the unreacted soaps in the lipid phase are reacted with an anolyte to generate free fatty acids. The carbon dioxide can be introduced as a gaseous flow of carbon dioxide into the reaction vessel. The carbon dioxide can be introduced as a gaseous flow of carbon dioxide into water and wherein the water is introduced to the reaction vessel. The generated free fatty acids can be separated, isolated, or purified into separate fractions. The mixed lipid feedstock can be selected from the group consisting of a soapstock, a washwater comprising soaps, and a combination thereof as generated during the chemical refining of a crude natural oil. The mixed lipid feedstock can be a tall oil soapstock. The crude natural oil can be a vegetable oil. The vegetable oil can be selected from the group consisting of soybean oil, canola oil, rapeseed oil, corn oil, rice oil, sunflower oil, peanut oil, sesame oil, palm oil, algae oil, jatropha oil, castor oil, safflower oil, grape seed oil, and any combination of vegetable oils. The mixed lipid feedstock can further comprise: water, soaps, phospholipids, saponifiable material, and unsaponifiable material. The organic acid can be carbonic acid. The carbonic acid can be generated by adding carbon dioxide to the saponification product mixture, thereby causing the carbon dioxide to react with the water in the saponification product mixture to form carbonic acid.

Another feature of the present invention is to provide a method for generating free fatty acids from a mixed lipid feedstock. The method comprising the following steps as described herein. The mixed lipid feedstock is provided. The mixed lipid feedstock is combined with a base to form a mixture. The mixture is allowed to react in a reaction vessel. Carbon dioxide is introduced into the reacted mixture in the reaction vessel to form a first carbonic acid within the reaction vessel. The first carbonic acid is mixed with the reacted mixture within the reaction vessel. The first carbonic acid and reacted mixture is allowed to settle within the reaction vessel. A first aqueous layer is drained from the reaction vessel. The collected first aqueous layer is treated with calcium oxides, magnesium oxides, barium oxides, or other polyvalent oxides. The method can further comprise the following steps as described herein. The treated collected first aqueous layer can be oxidized. The method can further comprise an electrolysis step wherein a lipid phase comprising a small amount of unreacted soaps is transferred to an electrolysis unit wherein the unreacted soaps in the lipid phase are reacted with an anolyte to generate free fatty acids.

Yet another feature of the present invention is to provide a method for generating free fatty acids from a mixed lipid feedstock. The method comprising the following steps as described herein. The mixed lipid feedstock is provided. The mixed lipid feedstock is combined with a base to form a mixture. The mixture is allowed to react in a reaction vessel. The reacted first mixture is combined with an organic or inorganic acid, thereby acidulating soaps in the first mixture to generate free fatty acids. The generated free fatty acids are combined with an alcohol to form a second mixture. The second mixture is heated and pressurized to above the critical temperature and pressure of the alcohol, thereby esterifying substantially all of the free fatty acids to generate fatty acid alkyl esters. The method can further comprise the following steps as described herein. The method can further comprise an electrolysis step wherein a lipid phase comprising a small amount of unreacted soaps is transferred to an electrolysis unit wherein the unreacted soaps in the lipid phase are reacted with an anolyte to generate free fatty acids. The organic acid can be a carbonic acid. The carbonic acid can be generated by adding carbon dioxide to the saponification product mixture, thereby causing the carbon dioxide to react with the water in the saponification product mixture to form a first carbonic acid. The carbon dioxide can be introduced as a gaseous flow of carbon dioxide into the reaction vessel. Carbon dioxide can be introduced into the reacted mixture in the reaction vessel to form a second carbonic acid within the reaction vessel. The second carbonic acid can be mixed with the reacted mixture within the reaction vessel. The second carbonic acid and reacted mixture can be allowed to settle within the reaction vessel. A second aqueous layer can be drained from the reaction vessel. Carbon dioxide can be introduced into the reacted mixture in the reaction vessel to form a third carbonic acid within the reaction vessel. The third carbonic acid can be mixed with the reacted mixture within the reaction vessel. The third carbonic acid and reacted mixture can be allowed to settle within the reaction vessel. A third aqueous layer can be drained from the reaction vessel. Hexane can be added to the reacted mixture in the reaction vessel after the draining of the third aqueous layer. Carbon dioxide can be introduced into the reacted mixture in the reaction vessel to form a fourth carbonic acid within the reaction vessel. The fourth carbonic acid can be mixed with the reacted mixture within the reaction vessel. The fourth carbonic acid and reacted mixture can be allowed to settle within the reaction vessel. A fourth aqueous layer can be drained from the reaction vessel.

Still yet another feature of the present invention is to provide a method for generating free fatty acids from a castor oil. The method comprising the following steps as described herein. The castor oil is provided. The castor oil is combined with a base to form a mixture. The mixture is allowed to react in a reaction vessel. Carbon dioxide is introduced into the reacted mixture in the reaction vessel to form a first carbonic acid within the reaction vessel. The first carbonic acid and the reacted mixture are mixed within the reaction vessel. The first carbonic acid and reacted mixture is allowed to settle within the reaction vessel. A first aqueous layer is drained from the reaction vessel. The method can further comprise the following steps as described herein. The carbon dioxide can be introduced as a gaseous flow of carbon dioxide into the reaction vessel. Carbon dioxide can be introduced into the reacted mixture in the reaction vessel to form a second carbonic acid within the reaction vessel. The second carbonic acid can be mixed with the reacted mixture within the reaction vessel. The second carbonic acid and reacted mixture can be allowed to settle within the reaction vessel. A second aqueous layer can be drained from the reaction vessel. Carbon dioxide can be introduced into the reacted mixture in the reaction vessel to form a third carbonic acid within the reaction vessel. The third carbonic acid can be mixed with the reacted mixture within the reaction vessel. The third carbonic acid and reacted mixture can be allowed to settle within the reaction vessel. A third aqueous layer can be drained from the reaction vessel. Hexane can be added to the reacted mixture in the reaction vessel after the draining of the third aqueous layer. Carbon dioxide can be introduced into the reacted mixture in the reaction vessel to form a fourth carbonic acid within the reaction vessel. The fourth carbonic acid can be mixed with the reacted mixture within the reaction vessel. The fourth carbonic acid and reacted mixture can be allowed to settle within the reaction vessel. A fourth aqueous layer can be drained from the reaction vessel.

Another feature of the present invention is to provide a method for generating free fatty acids from a mixed lipid feedstock. The method comprising the following steps as described herein. The mixed lipid feedstock is provided as step a). The mixed lipid feedstock is combined with a base to form a mixture as step b). The mixture is allowed to react in a reaction vessel as step c). Carbon dioxide is introduced into the reacted mixture in the reaction vessel to form a first carbonic acid within the reaction vessel as step d). The first carbonic acid is mixed with the reacted mixture within the reaction vessel as step e). The first carbonic acid and reacted mixture is allowed to settle within the reaction vessel as step f). A first aqueous layer is drained from the reaction vessel as step g). A generated lipid layer is removed from the reaction vessel as step h). Steps a) through h) are repeated above up to 8 times using the generated lipid layer from the reaction vessel as the mixed lipid feedstock for step a). The method can further comprise adding a salt to the generated lipid layer prior to any of the reactions. The salt can be sodium chloride. The method can further comprise adding sodium bisulfate to the generated lipid layer produced in any of the one or more reactions.

Yet another feature of the present invention is to provide a method for generating an animal feed additive from a mixed lipid feedstock. The method comprising the following steps as described herein. The mixed lipid feedstock is provided. The mixed lipid feedstock is combined with a base to form a first mixture. The first mixture is allowed to react. Carbon dioxide is introduced into the reacted mixture in the reaction vessel to form a first carbonic acid within the reaction vessel. The first carbonic acid is mixed with the reacted mixture within the reaction vessel. The first carbonic acid and reacted mixture are allowed to settle within the reaction vessel. A first aqueous layer is drained from the reaction vessel. The first aqueous layer is concentrated to generate a sodium bicarbonate product that is substantially free of any water, thereby generating an animal feed additive. The concentration step can further comprise using evaporation, fluidized bed drying, rotary drum drying, lyophilization, spray drying and reverse osmosis.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

FIG. 1 is a flow diagram of an exemplary method of the invention comprising generating free fatty acids and, optionally, fatty acid alkyl esters from a mixed lipid feedstock comprising soaps, saponifiable material or equivalents thereof.

Reference will now be made in detail to various exemplary embodiments of the invention. The following detailed description is provided to give the reader a better understanding of certain details of aspects and embodiments of the invention, and should not be interpreted as a limitation on the scope of the invention.

DETAILED DESCRIPTION OF THE INVENTION

In alternative embodiments, the invention provides processes for the preparation of fatty acids and optionally fatty acid derivatives, e.g. fatty acid alkyl esters, from mixed lipid feedstocks comprising saponifiable material, including byproduct streams of natural oil processing e.g. soapstocks, gums, or mixtures thereof. In alternative embodiments, the feedstock comprises soapstock obtained from the alkaline neutralization of a crude natural oil. In alternative embodiments, the feedstock comprises the gums product (comprising primarily phospholipids) generated during the degumming of a natural oil. In alternative embodiments, the feedstock comprises a mixture of product streams generated during the processing of crude natural oil and comprises soaps as well as saponifiable lipids, e.g. phospholipids glycerides, e.g. mono-, di-, and/or triglycerides, or any combination thereof. In alternative embodiments, processes of the invention are more economical and efficient than currently used approaches for the treatment of natural oil processing byproducts e.g. soapstocks and gums, to generate fatty acids, fatty acid derivatives, or other value-added products.

In alternative embodiments, a mixed lipid feedstock, e.g. a soapstock comprising soaps as well as saponifiable material (e.g. glycerides and/or phospholipids) is reacted with a base in a first saponification step to convert the saponifiable material to soaps (salts of fatty acids), thereby generating a product in which substantially all of the saponifiable material is converted to soaps. The soaps present in the product stream generated in the foregoing saponification step are then separated and reacted with an acid in a second acidulation step of the process in which substantially all of the soaps are acidulated to form free fatty acids (i.e. fatty acids with no ester moiety) and a salt, e.g. sodium bicarbonate if sodium hydroxide is the selected base used in the saponification step. Optionally, the free fatty acids are reacted with a supercritical alcohol in a third step of the process to generate fatty acid alkyl esters.

Crude (unrefined) natural oils, including plant- and animal-derived oils, are comprised primarily of triacylglycerols (i.e. triglycerides), as well as smaller portions of various lipids including mono- and diacyleglycerols, (i.e. monoglycerides and di-glycerides, respectively), free fatty acids, phospholipids, waxes, and other non-lipid components including, for example, ketones, aldehydes, and hydrocarbons. Prior to sale for human consumption or for further processing, a crude natural oil is usually refined to remove the majority of the non-triglyceride components. The majority of natural oils are refined using the chemical refining process. In the first stage of the chemical refining process, referred to as "degumming", crude oils are first washed with water to remove the hydratable phospholipids (gums). The resulting product stream separated from the oil during the degumming step is referred to as "gums." Second, the degummed oils are subjected to a neutralization step in which the degummed oil is treated with a strong base, e.g. sodium hydroxide. During the neutralization step, free fatty acids present in the oil react with the base to form soaps (salts of fatty acids). In some refineries, there is an additional processing step between the degumming and neutralization step in which a small amount of a mineral acid, e.g. phosphoric acid or citric acid) is added to the degummed oil to convert any non-hydratable phospholipids into hydrated phospholipids. After the neutralization step, the oil is washed to remove the soaps and, if the oil was treated with a mineral acid, the hydrated phospholipids. The resulting product stream separated from the oil during the neutralization step is referred to as "soapstock." If the oil is to be sold for human consumption, the degummed, neutralized oil is then subjected to further processing including, e.g. bleaching and deodorization steps.

Depending on the configuration of the refinery, soapstock and gums are either stored separately or combined into a single storage container. When referred to herein, a "mixed lipid feedstock" refers to any material or composition comprising soaps as well saponifiable material, i.e. lipids capable of reacting to produce soaps (salts of fatty acids). Saponifiable material in the mixed lipid feedstock can include, without limitation, glycerides, e.g. mono-glycerides, di-glycerides, or triglycerides, or a combination thereof, and/or phospholipids. In alternative embodiments, the mixed lipid feedstock is a soapstock. In alternative embodiments, the mixed lipid feedstock comprises soaps and saponifiable lipids e.g. glycerides and/or phospholipids. In alternative embodiments, the mixed lipid feedstock is a mixture of soapstocks, comprising soaps, saponifiable material, e.g. glycerides and/or phospholipids, obtained during the processing of a natural oil. In alternative embodiments, the mixed lipid feedstock is a soapstock washwater obtained from the processing of a crude natural oil following the neutralization step in the chemical refining process. In such embodiments, the washwater can comprise water and soapstock, wherein the soapstock comprises soaps, glycerides, phospholipids, free fatty acids, and unsaponifiable material e.g. waxes and/or sterols. In alternative embodiments, the soapstock washwater can comprise between about 1% soapstock to about 90% soapstock, e.g. between about 2% and 80% soapstock, about 3% and 70% soapstock, about 4% and about 60% soapstock, about 5% and about 50% soapstock, about 6% and about 40% soapstock, about 7% and about 30% soapstock, about 8% and about 20% soapstock, about 9% and about 15% soapstock, or between about 20% and about 12% soapstock, the remaining portion of the soapstock washwater comprising water. The composition of the soapstock used as a mixed lipid feedstock in accordance with the present invention can vary depending on the crude natural oil from which it was derived. Table 1 shows the composition of various soapstocks as described in U.S. Pat. No. 4,118,407.

TABLE 1

Composition of soapstocks from the refining of various natural oils

| Composition | Soybean | Cottonseed | Coconut | Palm Kernel | Palm |
|---|---|---|---|---|---|
| Water | 57.3 | 58.6 | 66.8 | 57.8 | 66.4 |
| Neutral Oil | 14.6 | 13.0 | 17.4 | 26.2 | 8.4 |
| FFA | 1.46 | 0.94 | 0.55 | 0.24 | 1.25 |
| Unsaponifiable | 1.1 | 1.4 | 0.85 | 0.38 | 0.2 |
| Soap | 14.2 | 17.5 | 14.4 | 14.2 | 23.8 |
| Phosphatide | 11.34 | 8.56 | 0 | 0 | 0 |
| Phosphorus | 0.8 | 0.38 | 0.16 | 0 | 0 |
| Total FFA | 23.7 | 27.6 | 27.3 | 38.1 | 21.9 |
| pH | 9.5 | 9.5 | 9.2 | 9.2 | 10.8 |

Other mixed lipid feedstocks suitable for use in the present process include tall oil soaps. Tall oil soaps are generated via the alkaline pulping of wood in the Kraft process. The alkaline pulping of wood using the Kraft process results in the production of black liquor, comprising the majority of the non-cellulose components of the wood. These products include hemicelluloses, lignin, and various salts of carboxylic acids including rosin salts and soaps (salts of fatty acids). After the black liquor is concentrated using multiple effect evaporators, it is allowed to settle or is centrifuged. As the concentrated black liquor settles, the soaps float to the surface where they are skimmed and removed. The skimmed product (referred to as black liquor soaps or tall oil soaps) is used as a feedstock in various embodiments of the process.

In alternative embodiments, the mixed lipid feedstock in the present process is a saponified crude natural oil, e.g. a saponified vegetable oil. In alternative embodiments, the mixed lipid feed feedstock is a saponified castor oil, i.e. a composition comprising soaps derived from mixing a base with a castor oil, the saponifiable content in the castor oil, e.g. glycerides, and phospholipids, having been converted to soaps. It is known in that the majority of the fatty acid content in castor oil (e.g. between 80 to about 95% of the fatty acid content) is ricinoleic acid (12-hydroxy-9-cz's-octadecenoic acid). In alternative embodiments, the invention provides methods or processes for generating ricinoleic acid by first saponifying a castor oil by adding a base, e.g. sodium hydroxide, to the castor oil, acidulating the saponified castor oil to generate free fatty acids, and then separating or isolating ricinoleic acid from the generated free fatty acids.

FIG. 1 shows an exemplary embodiment of the process (100) for generating free fatty acids and optionally fatty acid alkyl esters from a soapstock. A soapstock comprising soaps and unsaponified lipids (101) is first combined with a strong base, e.g. sodium hydroxide (102). The resulting combination is subjected to a saponification reaction (103) wherein substantially all of the saponifiable material in the soapstock (101) is converted to soaps (104), glycerol (105) and other products. Glycerol (105) is then separated from the soaps (104). The soaps (in water) (104), are then contacted with $CO_2$ (106), resulting in the formation of carbonic acid which acidulates the soaps in an acidulation reaction (107) to generate free fatty acids (109) and sodium carbonate salt (108). The free fatty acids (109) can optionally be combined with a solvent (110), e.g. a solvent comprising an alcohol (111) and an optional co-solvent (112), and reacted in an esterification reaction (113) at a temperature above the critical temperature of the alcohol and a pressure above the critical pressure of the alcohol to generate fatty acid alkyl esters (114).

Alternative embodiments of the methods and processes are described in greater detail bellow.

Soapstock Saponification:

In alternative embodiments, the first stage of the process is a saponification reaction with a mixed lipid feedstock. In alternative embodiments, a mixed lipid feedstock, e.g. a soapstock washwater comprising water, soaps as well as saponifiable material e.g. glycerides (e.g. mono- di- or triglycerides or any combination thereof) and phospholipids, is mixed with a base, e.g. a strong base such as sodium hydroxide or potassium hydroxide, and water to generate a saponification reaction mixture. The generated saponification reaction mixture is then allowed to react to convert substantially all of the saponifiable material in the mixed lipid feedstocks to soaps. During the saponification reaction, the base serves to cleave substantially all of the ester bonds of the saponifiable lipids present in the mixed lipid feedstock and the cation (e.g. sodium or potassium) joins the fatty acid molecule to form a salt of a fatty acid (soap). The resulting product comprises soaps as well as water-soluble material e.g. glycerol.

The following is a reaction scheme showing the saponification of a glyceride molecule in the mixed lipid feedstock in an exemplary embodiment of the present invention.

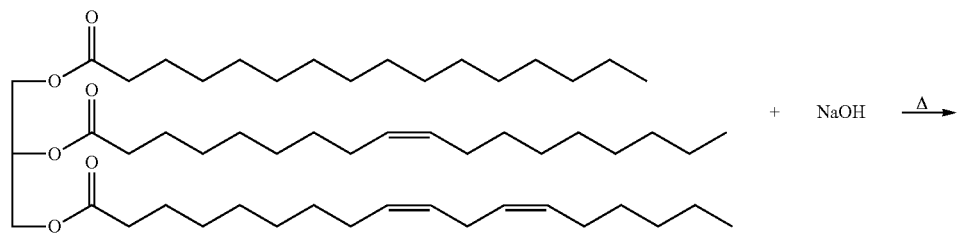

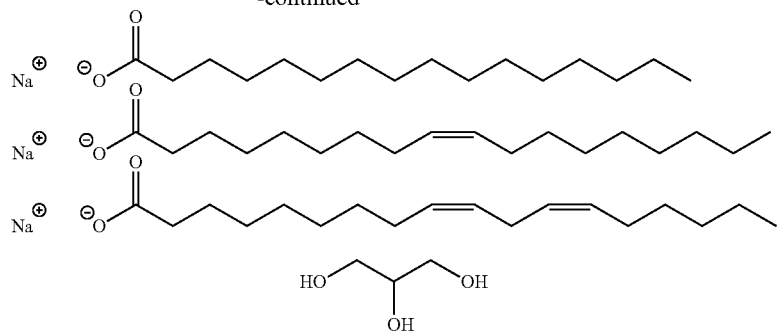

The following is a reaction scheme showing the saponification of a phospholipid molecule in the mixed lipid feedstock in an exemplary embodiment of the present invention.

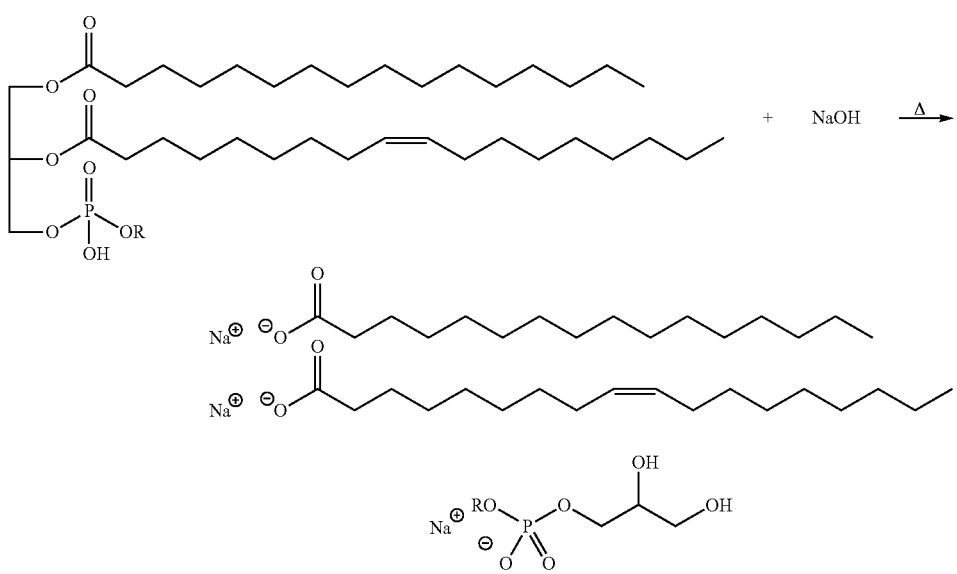

In alternative embodiments, the saponification reaction is carried out at a temperature in the range of between about room temperature (i.e. about 25° C.) to about 200° C., e.g. between about 50° C. to about 1 80° C., about 60° C. to about 160° C., about 70° C. to about 140° C., about 80° C. to about 120° C., or about 100° C. In alternative embodiments, the saponification reaction is carried out at a pressure of between about 0 to 100 psig, e.g. between about 5 and 50 psig, or between about 10 psig and 20 psig. In alternative embodiments, the saponification reaction is carried out at ambient pressure. In alternative embodiments, the amount of base in the saponification reaction mixture is between about 50 to 150% by weight of the dry weight of the mixed lipid feedstock (wt/wt %), e.g. about 100 wt/wt % of the dry weight of the mixed lipid feedstock.

In alternative embodiments, the base used in the saponification reaction is any base of hydroxide, e.g. sodium hydroxide (aOH) or potassium hydroxide (KOH). In alternative embodiments, the amount of base in the saponification reaction mixture is sufficient to increase the pH of the reaction mixture to a level that is sufficient to saponify substantially all of the saponifiable material in the mixed lipid feedstock, e.g. a sufficient amount of base to increase the pH of the saponification reaction mixture to a level greater than a pH of 10, e.g. a pH of 12. In alternative embodiments, the amount of water in the saponification reaction is between about 5:1 water-to-feedstock to about 10:1, e.g. about 6:1.

The saponification reaction can take place in any suitable reaction vessel known in the art. In alternative embodiments, the reaction can be a batch or continuous process, depending on the desired throughput of material from the reaction.

In alternative embodiments, the reaction products generated by the saponification reaction comprise soaps (salts of fatty acids), glycerol, phosphate salts as well as unsaponifable material e.g. waxes and sterols. In alternative embodiments, the product generated from the saponification reaction is an emulsification. The product mixture generated in the foregoing saponification reaction is referred to herein as the "saponification product mixture."

In certain embodiments, following the saponification reaction, the resulting reaction products (i.e. the saponification product mixture) are subjected to a separation step in which the soaps are separated from the reaming reaction products, e.g. glycerol. The separation step can be any suitable separation technique known in the art, e.g. filtration, centrifugation, water washing, or any combination of separation techniques. In an exemplary embodiment, the reaction products from the saponification step are allowed to settle and then the soaps are skimmed from the surface of the mixture. In alternative embodiments, the skimmed soaps are then subjected to a water wash in which substantially all of the non-soap material is removed from the soaps.

In other embodiments, the reaction product generated following the saponification product is an emulsion comprising, for example, soaps, water and unsaponifiable material e.g. waxes and sterols. In alternative embodiments, the emulsified saponification reaction product is not subjected to a subsequent separation step to separate the soaps from the other components of the reaction product. In certain embodiments, the acidulation reaction (described below) is carried out on the saponification reaction product in the same reaction vessel, without the saponification reaction product being subjected to a separation step or moved to a separate reaction vessel for the acidulation step of the process. In alternative embodiments, the reaction product generated during the saponification step of the process comprises between about 30% to about 90% water, e.g. between about 40% to about 70% water, or between about 50% to about 60% water.

Acidulation of Soaps:

In alternative embodiments, the soaps, or the reaction product generated during the saponification step of the process (i.e. the saponification product mixture), is subjected to an acidulation step in which substantially all of the soaps are acidulated to generate free fatty acids. The soaps are acidulated by mixing them, in any suitable reaction vessel, e.g. the same reaction vessel that was used in the saponification step, with an acid to form an acidulation reaction mixture. In alternative embodiments, the acid is an organic acid e.g. carbonic acid. In alternative embodiments, carbonic acid is generated by mixing $CO_2$, e.g. gaseous $CO_2$, with the saponification reaction product, wherein the $CO_2$ reacts with the water (present in the saponification reaction product) to form carbonic acid. In an exemplary embodiment, gaseous $CO_2$ is then piped or otherwise directed into the reaction vessel wherein the $CO_2$ reacts with the water present in the saponification reaction product to form carbonic acid. Once formed, the carbonic acid reacts with the soaps, thereby acidulating them and generating free fatty acids and a corresponding salt, e.g. sodium bicarbonate if sodium hydroxide (NaOH) was used as the base in the saponification step.

The amount of gaseous $CO_2$ used in the acidulation step of alternative embodiments of the process can vary depending on, for example, ambient temperature and pressure conditions, but is generally sufficient to increase the pressure of the reaction vessel in which the acidulation reaction is being carried out to between about 0 and about 800 psig, e.g. between about 10 and 700 psig, about 20 to about 600 psig, about 30 to about 500 psig, about 40 to about 400 psig, about 50 to about 300 psig, about 60 to about 200 psig, about 60 to about 150 psig, about 70 to about 140 psig, about 80 to about 120 psig, about 90 to about 110 psig, or about 100 psig. In alternative embodiments, the acidulation reaction is carried out at a temperature in the range of between about 5° C. to about 120° C., e.g. about 10° C. to about 90° C., about 15° C. to about 70° C., about 20° C. to about 60° C., or about 25° C. to about 40° C.

In alternative embodiments, the source of the gaseous $CO_2$ used in the acidulation step is a "stack gas" or "flue gas" (used interchangeably herein and referred to as "stack gas") other source of gaseous $CO_2$ emitted from an industrial process or any oven, furnace, boiler, steam generator or the like, e.g. from a coal fired power plant or any other industrial process wherein a gaseous waste stream comprising $CO_2$ is emitted. In alternative embodiments, the stack gas is piped or otherwise transferred from the emission source to the vessel in which the acidulation reaction is carried out. In alternative embodiments, the stack gas can comprise gaseous $CO_2$ and possibly other products depending on the filtration or other purification steps that the stack gas was subjected to prior to being transferred to the acidulation reactor. The exact composition of the stack gas will varying depending on the emission source and post-combustion processing steps but is generally comprised primarily of $CO_2$ (e.g. about 60% or more $CO_2$), nitrogenous products (e.g. $N_2O$ and $NO_2$), sulfur dioxide ($SO_2$), hydrogen sulfide ($H_2S$), water vapor and possibly other products.

In alternative embodiments wherein a stack gas is used as the $CO_2$ source, other products in the stack gas, e.g. $N_2O$, $NO_2$, $SO_2$, $H_2S$ or the like can react with the water in the acidulation reaction mixture to form their equivalent aqueous acid species (e.g., $SO_2$ would react with the water to generate sulfuric acid). The generation of additional acid products in the reaction mixture can serve to increase the reaction efficiency and reduce the total amount of time required to perform the acidulation reaction. As such, the use of a stack gas "waste stream" may be beneficial in the process, representing an opportunity to utilize a waste stream from one industrial process to benefit another industrial process (which might otherwise require expensive processing steps prior to being emitted) as an input for the present process. The process therefore is a means of diverting what would otherwise be an environmental pollutant to an input stream of a separate industrial process.

Other products may optionally be added to the acidulation reaction mixture e.g. organic or inorganic acids, e.g. formic acid or sodium bisulfate. The addition of additional acids can be useful in tailoring the ash profile of the resulting acidulation product mixture (the mixture of products resulting from the acidulation reaction) such that certain end products can be used as, e.g. a fertilizer. The optional addition of additional acids can serve to increase the reaction efficiency by acidulating soaps that were not acidulated by the carbonic acid.

In alternative embodiments, the desired pH of the acidulation reaction mixture is less than 5, e.g. 2 or 3. In alternative embodiments, the amount of $CO_2$ and optional other acids (e.g. from stack gas) added to the acidulation reaction mixture is sufficient to reduce the pH of the mixture to below 5 or about 2 or 3.

In alternative embodiments, flowing the addition of the $CO_2$ (or stack gas, or carbonated water) and optional other acids to the saponification reaction product and after the reaction vessel has reached the desired temperature and pressure to carry out the acidulation step, the resulting reaction mixture is agitated, or otherwise mixed in order to maximize the contacting of the soaps with the carbonic acid (generated once $CO_2$ reacts with the water present in the saponification reaction mixture). The mixture can be agitated using any suitable method known in the art, e.g. a spinning blade mixer. In alternative embodiments, the mixture is agitated for between about 10 minutes to about 60 minutes, e.g. between about 15 minutes to about 45 minutes, or between about 20 minutes to about 25 minutes, or about 30 minutes.

In alternative embodiments, following the agitation step, the contents of the acidulation reaction vessel are allowed to settle, allowing for the formation of a lipid layer and aqueous layer. The lipid layer floats on the top of the aqueous layer. In alternative embodiments, the lipid layer comprises free fatty acids and any non-acidulated soaps, and the aqueous layer comprises, for example, water, glycerol, phosphate salts, e.g. sodium phosphate if sodium hydroxide was the base used in the saponification step, sodium bicarbonate smaller amounts of sodium carbonate (or other equivalent salts if NaOH was not the base used in the saponification reaction), unsaponifiable material e.g. waxes and sterols, and dissolved carbonic acid. In alternative embodiments, the lipid layer comprising the free fatty acids generated in the acidulation reaction is separated from the remaining reaction products. The separation technique used can be any suitable separation technique known in the art. In alternative embodiments, the reaction products of the acidulation step are transferred to a separation vessel, e.g. a decanter wherein the mixture is allowed to settle and allowed to separate, forming an aqueous phase and a "lipid" phase comprising the free fatty acids which floats on top of the aqueous phase. In alternative embodiments, the decantation procedure results in the formation of separate lipid and aqueous phases in approximately 1 hour or less, depending on the configuration of the reaction vessel. Other separation techniques, e.g. centrifugation, may also be used in accordance with the present invention. In certain embodiments, the acidulation product mixture is not transferred to a separate vessel in order to separate the lipids from the remaining reaction products. In such embodiments, the aqueous layer is drained from the bottom of the reaction vessel and the lipid layer is recovered as the reaction product.

In alternative embodiments, the reaction products generated during the acidulation reaction are transferred to the separation unit in such a way that the loss of any gaseous C02 is minimized, e.g. via the use of a liquid level control feedback or other suitable method. In certain embodiments, after the acidulation reaction, the reaction vessel is depressurized, allowing for the dissolved carbonic acid to separate out of the solution as gaseous C02. In such embodiments, the captured C02 is recycled for use in the acidulation step.

In alternative embodiments, the process comprises multiple acidulation reactions. In such embodiments, following the first acidulation reaction as described above, the reaction vessel is depressurized and the gaseous C02 is captured and recycled. The lipid layer is then separated or otherwise removed from the aqueous layer, and water is added into the reaction vessel containing the lipid layer. Gaseous C02 is then added to the reaction vessel until the desired pressure is reached as described above. The reaction vessel is then heated and agitated as previously described and allowed to settle. The resulting lipid layer is then separated or otherwise removed from the aqueous layer as previously described. The resulting lipid layer is then separated or otherwise removed and can optionally be subjected to additional acidulation reactions as previously described, wherein additional water and C02 is added and the resulting mixture agitated at the desired temperature and pressure and the resulting lipid layer is separated or otherwise removed from the aqueous layer. The number of acidulation reactions in the process can vary depending on the desired free fatty acid yield and process economics. In certain embodiments, the number of acidulation reactions is sufficient to acidulate substantially all of the soaps present in the saponification product mixture, e.g. 3-8 acidulation reactions, e.g. 6 acidulation reactions.

In alternative embodiments, a salt, e.g. sodium chloride or other equivalent salt, is added to the product mixture following an acidulation reaction. The addition of NaCl or equivalent salt to the acidulation reaction product increases the ionic strength of the product mixture and prevents the lipid layer from emulsifying with the aqueous layer. In certain embodiments, the process comprises two or more acidulation reactions and the salt, e.g. NaCl, is added to the product mixture generated by the second acidulation reaction. In certain embodiments, the process comprises three or more acidulation reactions, e.g. six acidulation reactions, and the salt is added to the product mixture generated by the third acidulation reaction.

The acidulation reaction, or multiple acidulation reactions, can take place in any suitable reaction vessel known in the art. In alternative embodiments, the reaction can be a batch or continuous process, depending on the desired throughput of material from the reaction. In embodiments of the process comprising multiple acidulation reactions, the multiple acidulation reaction can take place in the same reaction vessel or in separate reaction vessels. In embodiments comprising multiple acidulation reactions taking place in multiple reaction vessels, the lipid layer generated during each acidulation reaction is separated or otherwise removed from the corresponding aqueous layer and transferred to a separate reaction vessel wherein the lipid layer is mixed with water and C02 and the resulting mixture is agitated for the desired period under the desired temperature and pressure conditions and allowed to settle in order to generate a new lipid layer.

In alternative embodiments, the separated free fatty acids generated in the acidulation reaction are subjected to further processing steps. In alternative embodiments, the free fatty acids are further separated by their carbon chain length, i.e. the number of carbon atoms contained in the aliphatic tail portion of the free fatty acid, which can comprise, in alternative embodiments, between 4 and 28 carbon atoms. In alternative embodiments, the free fatty acids are separated by their saturation. In alternative embodiments, the saturated free fatty acids are separated from the unsaturated free fatty acids. In alternative embodiments, the separated free fatty acids are separated into short-chain fatty acids (aliphatic tail length of fewer than 6 carbon atoms), medium-chain fatty acids (aliphatic tail lengths of between 6 and 12 carbon atoms), long-chain fatty acids (aliphatic tail length of between 13 and 21 carbon atoms), and very long-chain fatty acids (aliphatic tail length of 22 or more carbon atoms). In alternative embodiments, the separated free fatty acids are separated into individual fatty acids streams based on the length (number of carbon atoms) of their aliphatic tails.

In alternative embodiments, the separated free fatty acids can be further separated into distinct cuts, based on their aliphatic tail length and/or saturation, using any suitable technique known in the art, e.g. ion exchange, continuous ion exchange, chromatography, continuous chromatography or the like.

Electrolysis of Lipid Phase from Acidulation Reaction:

In alternative embodiments, the lipid phase having been separated in the foregoing acidulation reactions comprises a small percentage of unreacted soaps, i.e. soaps that were not acidulated to generate free fatty acids, e.g. between about 5 wt % and 20 wt %, or about 10 wt % of the lipid phase. In order to increase the overall efficiency of the process, alternative embodiments of the process comprise an electrolysis step wherein the lipid phase comprising a small amount of unreacted soaps is transferred to an electrolysis unit wherein the soaps in the lipid are reacted with an anolyte to generate free fatty acids. In alternative embodiments, the addition of the electrolysis step converts substantially all, e.g. 95% or more of the unreacted soaps to free fatty acids.

In alternative embodiments comprising the electrolysis step, the lipid layer from the acidulation reaction(s) is transferred to an electrolysis unit (e.g. a hydrogen evolving cathode (HEC) electrolysis unit) comprising a vessel or suitable container comprising an anode (the anode vessel) and a vessel or other suitable container comprising a cathode (the cathode vessel) separated by a selective filtration membrane, e.g. a polytetrafluoroethylene (PTFE) membrane. In alternative embodiments, the anode is comprised of a mixed metal oxide (MMO) layer coated onto a stable metal substrate, e.g. titanium. In alternative embodiments, the cathode can be, for example, titanium or a Monel alloy, or any other substrate that is stable in a reducing environment.

In alternative embodiments, a solution comprising an anolyte is added to the anode vessel. In alternative embodiments the anolyte is a sodium salt, e.g. sodium sulfate (for illustrative purposes, sodium sulfate is the anolyte in the remaining description of the electrolysis step, although those skilled in the art would appreciate that an equivalent anlolyte may be substituted in the process). Simultaneously, the cathode vessel is filled with a catholyte, e.g. sodium hydroxide. In alternative embodiments, a current is passed through the electrolysis unit resulting in the oxidation of the sodium sulfate, thereby generating sodium ions and sodium bisulfate. The current also serves to oxidize the water, generating hydrogen ions. The generated sodium ions are pushed across the electrolysis membrane and the generated sodium bisulfate results in a reduction of the pH of the anolyte solution to, e.g. about 3. Once the pH has reached a suitable level, e.g. about 3, a portion of the separated lipid from the acidulation step is introduced into the vessel with the anolyte solution wherein any unreacted soaps in the lipid layer react with the sodium bisulfate to generate free fatty acids and sodium sulfate. The generated free fatty acids are separated from the anode vessel by any suitable method in the art, e.g. through a pipe at the top of the anode vessel and into separate side tank. The generated sodium sulfate acts as the regenerated anolyte which, after the fatty acids have been removed from the anode vessel, is oxidized by passing a current through the anode. As such, the electrolysis unit operates in a semi-continuous fashion, wherein sodium sulfate is oxidized to generate sodium bisulfate, thereby lowering the pH of the anolyte solution. Once the pH has reached a suitable level, e.g. about 3 additional lipid material from the acidulation reaction step is added, and the soaps present in the lipid material react with the sodium bisulfate to generate free fatty acids and sodium sulfate.

As the electrical current is passed through the cathode, the water is reduced, thereby generating hydroxide ions. As the sodium ions are pushed across the membrane from the anode vessel into the cathode vessel, they react with the generated hydroxide ions to generate sodium hydroxide. In alternative embodiments, the starting concentration of the catholyte (sodium hydroxide) is about 30 wt %. As additional sodium hydroxide is generated (from the sodium ions moving across the membrane and into the cathode and reacting with the hydroxide ions), the concentration of sodium hydroxide increase to, e.g. about 33 wt % before some of the sodium hydroxide is removed to bring the concentration back down to its original concentration, e.g. 30 wt %. The generated sodium hydroxide solution comprising sodium hydroxide and water can be recycled for use in the saponification reaction, resulting in a more "closed loop" system.

In alternative embodiments, the electrolysis unit is a hydrogen evolving cathode (HEC) unit with a current density in the range of about 1-10 kA/m2. In alternative embodiments, the voltage of the individual cells of the unit can be in the range of between about 3 and 15 volts. In alternative embodiments, the unit comprises holding tanks for the anolyte and catholyte for electrolyte balancing as the process is carried out. In alternative embodiments, the holding tank of the catholyte also serves as the additional tank for the lipid product, as well as a decanter for separating fatty acids generated in the process. In alternative embodiments, upon startup of the electrolysis unit, the sodium sulfate anolyte is electrolyzed, causing the pH of the anolyte solution to drop from, e.g. about 7 to about 3 to 3.5 and the temperature of the anode vessel is increased to between about 40-90° C., or above the melting point of the lipid solution entering the anode. In alternative embodiments, the lipid product is added to the anolyte solution until the pH increases to, e.g. about 4.5, after which point the addition of the lipid product is halted. In alternative embodiments, once the anolyte is electrolyzed, it contacts the soaps, which floats in the holding tank/decanter due to limited solubility in the anolyte. Once the pH in the anolyste solution is reduced to 3-3.5, the circulating pump halts and fatty acid is decanted from the anolyte for downstream processing.

In alternative embodiments, the foregoing electrolysis procedure is used as a total replacement of the acidulation reaction comprising acidulating soaps using carbonic acid. In such embodiments, the saponification product mixture generated in the saponification reaction is subjected to electrolysis as described above, wherein the product entering the anode vessel of the electrolysis unit is the saponification product mixture rather than the lipid layer separated from the acidulation product mixture.

Treatment of Aqueous Phase from Acidulation Reaction: Evaporation/Drying

In alternative embodiments, the aqueous phase(s) generated in the one or more acidulation reactions is subjected to one or more processing steps in order to recover desirable reaction products that remain in the aqueous phase of the acidulation reaction products and/or to treat the aqueous phase such that the resulting product meets or exceeds relevant regulatory standards relating to animal feed additives.

In alternative embodiments, the aqueous phase, or multiple aqueous phases (i.e. collected from acidulation reactions) is treated to remove water, e.g. by any suitable drying method (e.g. evaporation via falling film, forced recirculation flashing, or any other suitable method) known in the art, thereby generating a product comprising sodium biconrbonate. Care must be taken so as not to convert sodium bicarbonate to sodium carbonate via thermal degradation, so evaporation temperature should be conducted below about 60° C. and should be conducted under a vacuum.

In alternative embodiments, once a majority of the water has been removed from the aqueous stream(s), the resulting product can be dried further to generate a sodium bicarbonate product that is substantially free of any water, e.g. less than about 20% water or less than about 10% water. Suitable apparatuses for creating a substantially dry sodium bicarbonate product include fluidized bed dryers, lyophilizers, spray dryers, and rotary drum dryers. The generated dried sodium bicarbonate product can be used in any application that utilizes a crude sodium bicarbonate stream, e.g. as an animal feed additive.

Filtration

In alternative embodiments, the aqueous phase(s) generated in the one or more acidulation reactions is subjected to one or more processing steps in order to recover desirable reaction products that remain in the aqueous phase of the acidulation reaction products and/or to treat the aqueous phase such that the resulting product meets or exceeds relevant regulatory standards relating to wastewater. In alternative embodiments, the aqueous phase(s) generated during the one or more acidulation reactions can comprise various organic molecules and salts in addition to water. The exact composition of the aqueous phase(s) will vary depending on the feedstock used in the process, as well as other process variables, e.g. the reaction conditions, separation technique to separate the lipid phase from the aqueous phase during the acidulation process, etc. In alternative embodiments, the aqueous phase(s) may include, in addition to water: sodium bicarbonate (or equivalent salt if a base other than sodium hydroxide was used in the saponification step), glycerol, phosphates, cholines, ethanolamines, sodium sulfate (or equivalent salt), inositol, unreacted saponifiable material, e.g. soaps and/or glycerides, residual (small amounts of) free fatty acids, other organic or inorganic compounds, or any combination thereof.

The composition of an exemplary aqueous phase generated in the acidulation step comprising 6 acidulation reactions, wherein the feedstock of the process is a soapstock obtained from the processing of a crude soybean oil, is described below:

water 92.8%
sodium sulfate 1.4%
glycerin 0.79%
choline 0.06%
ethanolamine 0.02%
inositol 0.05%
phosphate 0.12%
sodium bicarbonate 4.72%

In alternative embodiments, the aqueous phase(s) may be treated using filtration, e.g. a size-exclusion filtration system. In alternative embodiments, the filtration step may be operationally in-line (i.e. continuously) with the acidulation step such that aqueous phase generated in each acidulation reaction (if the embodiment comprises more than one acidulation reaction) is treated immediately after or during the point at which the aqueous phase is separated from the lipid phase. In other embodiments, the aqueous phases may be collected and treated in a single batch.

In alternative embodiments, wherein the process comprises multiple acidulation reactions, the aqueous phase generated in each of the acidulation reactions is continuously pumped through a filtration mechanism, e.g. a nano- or microfiltration system or other appropriate membrane filtration system which may be selected from any of the known nano-, micro- or other appropriate size-exclusion filtration mechanisms or systems known in the art.

In alternative embodiments, the size of the pores of the filter allows for the rejection (i.e. allows the particles to pass through the membrane) of certain particles, e.g. soaps and/or phosphates, and retains (i.e. does not allow the particles to pass through the membrane) the sodium bicarbonate (or other equivalent salt if sodium hydroxide was not the salt used in the saponification reaction step). In alternative embodiments, the particles that pass through the membrane of the filter have a molecular weight less than the molecular weight of sodium palmitate, e.g. sodium bicarbonate, sodium phosphates, etc. In alternative embodiments, rejected particles are sodium (or other equivalent) soaps, e.g. sodium palmitate, sodium pleate, etc. In alternative embodiments, the filtration system provides for a more efficient process in that the soaps and/or other saponifiable material rejected by the membrane of the filter are returned to the lipid phase for subsequent acidulation reactions, thereby increasing the overall fatty acid yield of the process.

In alternative embodiments, the addition of a filtration step in the process serves to drive the acidulation reaction to completion be removing the sodium bicarbonate (or other equivalent salt) from the acidulation product. Sodium bicarbonate can "back-react" with the fatty acids generated in the acidulation step, wherein some of the fatty acids react with the sodium bicarbonate to generate soaps, thereby lowering the overall fatty acid yield of the process. By removing the generated sodium bicarbonate from the acidulation products, the opportunity for back-reacting with the sodium bicarbonate is diminished and the fatty acid yield of the process is increased.

In alternative embodiments, the filtration step is carried out in a pH range of between about 6 and 11 and a pressure of between about 50 and 800 psi, while maintaining a temperature of between about 23 and 100° C. In alternative embodiments, the pH of the acidulation product solution on which the filtration step is carried out varies depending on the amount of sodium bicarbonate in the solution. As the sodium bicarbonate is removed, e.g. via filtration, the pH drops and becomes increasingly acidic, thereby driving the acidulation reaction to completion. In alternative embodiments, the aqueous phase of the acidulation reaction(s) is pumped through the filter at a range of between about 1 and 100 gallons per minute. In alternative embodiments, the size of the pores in the filter membrane has a molecular weight cutoff (MWCO) of between about 100-250 Daltons.

In alternative embodiments, the retained portion of the aqueous phase comprising the sodium bicarbonate (or other equivalent salt if sodium hydroxide was not used in the saponification reaction step) is then subjected to a concentration step using, for example, reverse osmosis (RO). In alternative embodiments, the conditions for the RO step are similar to those of the filtration step, i.e. a pH in the range of between about 6 and 11, a pressure of between about 50 and 800 psi, while maintaining a temperature of between about 23 and 100° C. In alternative embodiments, the concentrated sodium hydroxide can be discarded or sold, increasing the overall efficiency of the process. In alternative embodiments, the water produced in the RO step is suitable pure to be recycled within the acidulation step, thereby increasing the efficiency of the process and reducing total water consumption.

Lime Treatment and Oxidation of Organics

In alternative embodiments, the aqueous phase generated in the acidulation reaction, or multiple acidulation reactions, is collected and contacted with calcium hydroxide, i.e. slaked lime. The amount of lime added to the aqueous phase is generally an amount sufficient to increase the pH of the solution to about 11. The lime-treated aqueous phase is allowed to react for a period of between about 1 and 24 hours. During the reaction time, various precipitates form and the pH of the solution increases to about 12 or 13. In alternative embodiments, wherein sodium hydroxide is the base used in the saponification step, an ion-swap occurs between the lime and sodium bicarbonate in the aqueous phase, thereby regenerating the sodium hydroxide for recycling in the saponification step of the process.

In the same lime-contacting step described above, various calcium precipitates are formed when they react with various components in the aqueous phase. These precipitates can include, for example, various calcium phosphates (i.e. Cax (P04)x). Other components of the lime-treated aqueous phase can include, for example, those products that were present in the recovered aqueous phase of the one or more acidulation reactions that did not react with the lime, e.g. glycerol, ethanolamines, choline, other organics, or any combination thereof.

In order to satisfy the Biochemical Oxygen Demand requirements for conventional wastewater treatment facilities, in alternative embodiments, the lime-treated aqueous phase product may be subjected to an oxidation step in which the organics present in the solution, e.g. phosphorous, glycerin, and other organics are fully oxidized into gaseous products that precipitate out of solution. In alternative embodiments, the lime-treated aqueous phase is subjected to Fenton oxidation wherein hydrogen peroxide and Fe2+ ions are used to catalyze OH radical formation. In alternative embodiments, the Fenton oxidation step is carried out by adding between about 1 and 10 grams of hydrogen peroxide per liter of aqueous phase liquid and between about 0.1 and 1.0 mol Fe2+ per mol of hydrogen peroxide to the lime-treated aqueous phase. The resulting mixture is then allowed to react for between about 1 and 24 hours at a temperature of between about 20-50° C. Once the hydrogen peroxide and Fe2+ are added to the lime-treated aqueous phase, the pH will drop rapidly to between about 3 and 9, e.g. less than pH 7. The pH then rises slowly as the organics are gasified and leave the solution. The reaction is considered complete when the rate of change in the pH of the solution is less than about 0.1 units/hour. UV oxidation can optionally be used in combination with Fenton oxidation.

In alternative embodiments, following the oxidation step, the solution is then contacted with fresh lime to precipitate any unbound phosphorus and other acidic species. The conditions for the second lime treatment step are identical to those of the first lime treatment step.

In alternative embodiments, following the second lime treatment step, the regenerated sodium hydroxide (NaOH) can be concentrated for recycling and use in the saponification step of the process. The amount of water that must be removed from the solution comprising the NaOH will depend on the amount of water required for the saponification step. Therefore, if the NaOH is to be recycled in the process, it is not necessary to remove all of the water from the NaOH. This can be achieved using any methods known in the art, e.g. evaporation, reverse osmosis, or the like.

Esterification of Free Fatty Acids:

In alternative embodiments, the free fatty acids generated in the acidulation reaction are optionally subjected to an esterification step in which substantially all of the free fatty acids are esterified to form fatty acid alkyl esters. In alternative embodiments, the esterification is carried out by mixing the free fatty acids with an alcohol and subjecting the resulting reaction mixture to a temperature above the critical point of the alcohol and a pressure above the critical pressure of the alcohol, thereby causing the alcohol to become supercritical. In its supercritical state, the alcohol reacts with the free fatty acids to form an ester product of fatty acid alkyl esters. The alcohol used in the esterification step can be an alcohol with between 1 and 5 carbons. In alternative embodiments, the alcohol is methanol or ethanol.

In alternative embodiments, the esterification step comprises a first emulsification step. The emulsification step can be carried out using any suitable technique known in the art. In alternative embodiments, the emulsification is carried out by combining the free fatty acids with the alcohol and subjecting the resulting mixture to a high mechanical sheer. The sheer time can be in the range of between about 1 and 100 minutes, or until an emulsification is formed. The molar ratio free fatty acids to alcohol in the reaction mixture for the esterification step can be between about 1:1 to about 1:30, e.g. about 1:10.

In alternative embodiments, after the emulsification is formed, it is transferred to a reaction vessel wherein it is subjected to temperatures and pressures above the critical point of the alcohol. The reaction vessel can be any suitable reaction vessel capable of withstanding the temperatures and pressures necessary to allow the alcohol to become supercritical. The reaction can be batch or continuous, depending on the desired throughput. In alternative embodiments, the emulsification of the fatty acids and alcohol are pumped into a continuous, plug-flow, continuously stirred tanks, batch-type, or other suitable reaction vessel. In alternative embodiments, the temperature in the reaction vessel is between about 235° C. to about 375° C. and the pressure is between about 500-5000 psig. In certain embodiments, the alcohol used in the esterification step is methanol. In such embodiments, the temperature in the reaction vessel is above the critical temperature of methanol, or above about 240° C., and the pressure in the reaction vessel is above the critical pressure of methanol, or above about 1172 psig. In certain embodiments, the alcohol used in the esterification step is ethanol. In such embodiments, the temperature in the reaction vessel is above the critical temperature of ethanol, or above about 240° C., and the pressure in the reaction vessel is above the critical pressure of methanol, or above about 890 psig. The reaction time can be between about 10 seconds to about 5 hours, or sufficiently long to allow for the esterification of substantially all of the free fatty acids, e.g. between about 1 minute and about 4 hours, about 20 minutes and about 3 hours, about 30 minutes and about 2 hours, or about 40 minutes and about 90 minutes, or about 60 minutes and about 75 minutes.

In alternative embodiments, a co-solvent can optionally be included in the reaction mixture in the esterification step. The additional of a co-solvent can allow for increased miscibility of the free fatty acids in the alcohol and can result in decreased reaction times to affect complete conversion of free fatty acids to fatty acid alkyl esters. The co-solvent can be, for example, an organic acid or a hydrocarbon, or combinations thereof. Suitable hydrocarbon co-solvents include, without limitation, ethane, propane, butane, and hexane, or combinations thereof. Suitable organic acid co-solvents include, without limitation, formic acid, acetic acid, propionic acid, butyric acid, valeric acid, caprionic acid, oxalic acid, lactic acid, malic acid, citric acid, benzoic acid, carbonic acid, or any combination thereof.

In alternative embodiments, the product mixture following the esterification reaction comprises fatty acid alkyl esters, unreacted alcohol, water, and, if present in the reaction mixture, co-solvent. If methanol was the alcohol used in the esterification reaction, the fatty acid alkyl esters will be fatty acid methyl esters (FAME). If ethanol is used in the esterification reaction, the fatty acid alkyl esters will be fatty acid ethyl esters (FAEE).

The reacted material from the esterification reaction (i.e. the product mixture in which the fatty acids are substantially esterified) is passed through a high pressure heat exchanger, e.g. a plate, shell and tube, concentric, spiral, or other suitable heat exchanger, wherein heat is withdrawn from the product mixture and optionally recovered (where the heat can be recycled for use elsewhere in the process, e.g. to heat the reactor used in the esterification step, thereby decreasing the overall energy requirements of the system).

In alternative embodiments, the heat recovery is conducted under pressure, e.g. at approximately 50 psi below the pressure of the initial reaction, thus, the temperature of the product mixture from which heat is being transferred can be reduced to below the supercritical point of the alcohol (e.g. methanol, which has a supercritical point of 240° C., so the heat is reduced to below 240° C.) while maintaining a pressure above its critical pressure (e.g. above about 1172 psi), thereby keeping the solvent, e.g. methanol, in a hot compressed liquid (non-vapor) state. In this alternative embodiment, the product mixture maintains a relatively thin (i.e. non-viscous) consistency, allowing for a high Log Mean Temperature Differential and Heat Transfer Coefficient, thereby reducing the total amount of contact area necessary to achieve the desired heat transfer.

In alternative embodiments, the reactor is heated using an oil, where optionally the oil can be heated by burning a natural gas, and the heat can be recovered by reducing the temperature of the product mixture from, for example, 285° C. to 215° C. (using the methanol as the alcohol example), or equivalent for other solvents, which allows a reduction in the amount of energy (e.g. natural gas) needed to heat the heating oil by approximately 30%. In alternative embodiments the heat transfer process reduces the temperature of the product mixture to, e.g. about 215° C. for the methanol as an exemplary alcohol.

In alternative embodiments, the temperature of the reaction mixture is not lowered to a temperature such that a significant portion of the alcohol, e.g. methanol, remains with the other components of the product mixture during the alcohol, e.g. methanol, recovery step. For example, if the amount of heat recovered resulted in a reduction in temperature of the product mixture to about 180-190° C., the amount of methanol that remains with the product mixture following the alcohol (e.g. methanol) recovery step would be in the range of about 10 wt %. By maintaining a temperature of about 215° C., the amount of alcohol (e.g. methanol) remaining in the product mixture following the alcohol (e.g. methanol) recovery step is approximately 2 wt %.

In alternative embodiments, following the heat recovery step, the product mixture undergoes a flash process wherein the product mixture is transferred to a flash drum or appropriate or equivalent vessel wherein the pressure is reduced from the pressure within the heat exchanger, e.g. above 1171 psi or about 1200 psi, to, for example, about atmospheric pressure, or about less than 14 psi, e.g. less than 1 psi, or about 0.1 psi. The decrease in pressure results in an environment in which the vapor pressure of the alcohol, e.g. methanol, exceeds its external pressure (the pressure of the flash drum or vessel), allowing for the alcohol, e.g. methanol, water, and, if present, the co-solvent (collectively referred to as the "solvent") to vaporize or "flash" out of the product mixture.

A flash at 0.1 psi results in approximately 95% of solvent present in the product mixture to vaporize and leave the flash vessel, with approximately 5% of the solvent remaining in a liquid state and existing in the bottom of the flash unit along with the remaining products in the product mixture (i.e. the "ester stream" comprising the fatty acid alkyl esters). In such embodiments, the concentration of solvent (i.e. alcohol, water and, if present, co-solvent) leaving the flash unit in a liquid state (in the ester stream) is approximately 2 wt % of the ester stream.

In alternative embodiments, the ester stream leaves the flash unit at a temperature in the range of between about 110 to about 125° C., e.g. 115° C. and is sent to a heat exchanger, e.g. a standard shell and tube heat exchanger, wherein it is cooled to about 95° C. The recovered heat can be recycled for use in the process, e.g. to heat the reactor.

In alternative embodiments the solvent (alcohol, water and, if present, co-solvent) mixture that was flashed in a previous step, wherein the mixture (if no co-solvent was included in the esterification reaction) is approximately 95 wt % methanol and 5 wt % water, is then distilled to yield a substantially pure alcohol, e.g. methanol product, e.g. approximately 99.8% or more alcohol, e.g. methanol. The substantially pure alcohol, e.g. methanol, product can be recycled for use in subsequent reactions.

In alternative embodiments, the ester stream (i.e. the "bottoms" from the previous liquid-vapor separation step comprising primarily fatty acid alkyl esters as well as some small amount of unreacted fatty acids as well as any of the solvent that was not removed in the previous liquid-vapor separation step) is heated to a temperature in the range of between about 120 to about 250° C., e.g. between about 180 to about 190° C. and transferred to a liquid-vapor separation unit, e.g. a flash chamber, under a vacuum range of between about 5 to about 750 Torr, causing any remaining solvent that was not separated from the esterification product mixture in the previous liquid-vapor separation step to vaporize and evaporate off of the remaining "bottoms", i.e. the fatty acid alkyl esters and unreacted fatty acids. The separated solvent can then be purified as described in the previous distillation step to yield a substantially pure alcohol, e.g. methanol product, e.g. approximately 99.8% or more alcohol, e.g. methanol. The substantially pure alcohol, e.g. methanol, product can be recycled for use in subsequent reactions.

In alternative embodiments, the ester stream, i.e. the material that did not evaporate in the previous liquid-vapor separation step, wherein substantially all of the solvent has been removed, is then distilled to generate a product stream comprising substantially purified, i.e. comprising between about 90 and about 99.8 percent fatty acid alkyl esters, e.g. 91%, 92%, 93%, 94%, 95%, 96%, 97%, 98%, 99%, or more, fatty acid alkyl esters, e.g. FAME. In alternative embodiments, the ester stream is purified by transferring the ester stream to a distillation column, e.g. a packed or trayed distillation column, under vacuum of between about 1 to about 200 Torr and heated to a temperature of between about 0 to about 300° C., e.g. about 250° C. The resulting distillate stream is comprised substantially purified, e.g. 99.8%) or more, fatty acid alkyl esters. The "bottoms" of the distillation column are then optionally transferred to a second distillation column in which the pressure is in the range of about 0.05 to about 100 Torr, causing substantially all of the free fatty acids to evaporate. The separated free fatty acids can optionally be recycled in the process in subsequent esterification reactions.

EXAMPLES

Example 1

Saponification and Acidulation of Soapstock

This example describes an exemplary protocol of the invention:

Soybean oil Soapstock Makeup generated was obtained from a natural oil refining facility and was used as a feedstock to generate free fatty acids (FFAs). The feedstock was first subjected to a saponification reaction to convert the saponifiable material in the feedstock to soaps. The product resulting from the saponification reaction was then subjected to an acidulation reaction wherein C02 was introduced into the reaction vessel comprising the saponification product. The C02 reacted with the water in the saponification product to form carbonic acid and acidulated soaps, thereby generating an acidulation reaction product comprising a first lipid layer comprising free fatty acids and a second aqueous layer comprising water glycerol, sodium bicarbonate, unsaponifiable material, e.g. waxes and sterols, dissolved carbonic acid, and phosphate salts.

Feedstock Description:

The feedstock used in the present example was 55 gallons of soybean oil Soapstock Makeup obtained from a natural oil refinery. The crude soybean oil was processed using the conventional chemical refining process for treating crude natural oil. First, phosphoric acid was added to the crude soybean oil in order make the phospholipids (gums) soluble in water. Second, the crude soybean oil was treated with sodium hydroxide to neutralize the majority of free fatty acids. During the neutralization process, the free fatty acids reacted with the sodium hydroxide to form soaps sodium salts of fatty acids). Water was then added to neutralized oil in order to dissolve the soaps and gums and the oil was centrifuged to remove the majority phospholipids (gums) and the soaps. The oil is then washed with water to remove any excess soap and sodium hydroxide in the oil. The resulting waterwash material is referred to herein as the Soapstock Makeup, which was the feedstock in the present example. In addition to soaps and gums, the feedstock comprised various saponifiable material including mono-, di-, and triglycerides.

Composition of Feedstock:

55 gallons Soapstock Makeup: 12 wt % Soapstock (Soaps, saponifiable material, and unsaponifiable material), and 88 wt % water.

Saponification Reaction:

55 gallons of Soapstock Makeup and 10 lbs. of 50 wt % NaOH (referred to collectively as the "reaction mixture") were placed in a 75 gallon jacketed (insulated) reaction vessel. The reaction mixture was agitated using a spinning blade mixer at 232 rpm. The temperature of the reaction vessel was increased to 100° C. and reacted for 4 hours at atmospheric pressure to allow for complete conversion of substantially all saponifiable material in the soapstock to soaps. The resulting product mixture was an emulsification comprising soaps, water, and unsaponifiable material.

Acidulation Reaction:

First acidulation reaction: After the saponification reaction, gaseous C02 was slowly introduced into the sealed reaction vessel through a port located near the bottom of the vessel. C02 was continually added to the reaction vessel until the pressure inside the vessel reached 100 psig. The reaction vessel was maintained at a temperature of 95° C. and agitated using a spinning blade mixer spinning at 232 rpms for a period of 30 minutes. After 30 minutes, the contents of the reaction vessel were allowed to settle for 10 minutes. During settling, a lipid layer and an aqueous layer formed and the lipid layer floated on top of the aqueous layer. The aqueous layer was drained from the bottom of the reaction vessel. The total weight of the drained aqueous layer was 250 lbs.

Second acidulation reaction: After the aqueous layer was removed following the first acidulation reaction, the reaction vessel was depressurized to 20 psig. The contents in the reaction vessel were agitated using the spinning blade mixer as 250 lbs. of tap water was simultaneously introduced through the top of the reaction vessel. C02 was continually added to the reaction vessel until the pressure inside the vessel reached 100 psig. The reaction vessel was maintained at a temperature of 95° C. and agitated using the spinning blade mixer at 232 rpms for a period of 30 minutes. After 30 minutes, the contents of the reaction vessel were allowed to settle for 10 minutes. During settling, a lipid layer and an aqueous layer formed and the lipid layer floated on top of the aqueous layer. The aqueous layer was drained from the bottom of the reaction vessel. The total weight of the drained aqueous layer was 290 lbs.

Third acidulation reaction: After the brine was removed following the second acidulation reaction, the reaction vessel was depressurized to 20 psig. The contents in the reaction vessel were agitated using the spinning blade mixer as 290 lbs. of 10 wt % aq. NaCl was simultaneously introduced through the top of the reaction vessel. C02 was continually added to the reaction vessel until the pressure inside the vessel reached 100 psig. The reaction vessel was maintained at a temperature of 95° C. and agitated using the spinning blade mixer at 232 rpms for a period of 30 minutes. After 30 minutes, the contents of the reaction vessel were allowed to settle for 10 minutes. During settling, a lipid layer and an aqueous layer formed and the lipid layer floated on top of the aqueous layer. The aqueous layer was drained from the bottom of the reaction vessel. The total volume of the drained aqueous layer was 20 gallons.

The contents of the reaction vessel were allowed to cool to a temperature of 65° C. 20 gallons of hexane was added to the reaction vessel in order to ensure that all lipids in the product mixture would separate from the aqueous layer. C02 was continually added to the reaction vessel until the pressure inside the vessel reached 100 psig. The reaction vessel was maintained at a temperature of 65° C. and agitated using the spinning blade mixer at 232 rpms for a period of 30 minutes. After 30 minutes, the contents of the reaction vessel were allowed to settle for 10 minutes. During settling, a hexane layer comprising the lipids (free fatty acids) was formed and floated on top of the product mixture. The reaction vessel was then allowed to drain from the bottom until the lipid layer was reached.

Analysis of FFA Content and FFA Profile:

Following the third acidulation reaction, a sample of the hexane layer comprising the free fatty acids (FFAs) was removed from the reaction vessel for analysis. First, the hexane was removed from the sample. Using acid titration, it was determined that the fatty acid content of the sample was 79.2 wt % FFA. The remainder of the sample was comprised of unacidulated soaps and various unsaponifiable material. The fatty acid profile of the sample is shown is Table 2.

TABLE 3

Summary results of acidulation reactions

| Reaction No. | pH | Weight of aqueous phase (lbs) | Total Dissolved Solids (%) |
| --- | --- | --- | --- |
| 1 | 8.55 | 232 | 25 |
| 2 | 7.82 | 363 | 7 |
| 3 | 7.67 | 476 | 3 |
| 4 | 7.11 | 539 | 1 |
| 5 | 6.79 | 596 | 0.5 |
| 6 | 5.98 | 537 | 0.5 |

Example 2

Conversion of 150 Gallons of Soapstock to Free Fatty Acids 443 lbs of soybean soapstock having a moisture content of 53.7% and a total fatty acid (TFA) content of 30.3% were added to a 150 gallon Inconel 600 batch-type reactor reactor with a three-tier agitator.

Saponification:

It was assumed that the TFA content was ⅓ phospholipid, ⅓ neutral oil, and ⅓ fatty soaps. As such, 56 lbs of 50 wt % NaOH was added to the reaction vessel and allowed to react at 95° C. for 2 hours while being agitated using a spinning blade agitator unit at 80 rpm. Following the saponification reaction, several 100-300 g samples of the saponified material was taken in triplicate and fully acidulated using sulfurinc acid to determine maximum TFA of wet saponified soapstock for use in subsequent mass balance calculations. It was determined that the average wet TFA content of the saponified soapstock was 19.5%.

Acidulation:

The saponified soapstock material was acidulated in six separate aciduation steps using 300 psig C02 and agitated at 80 rpm. Each acidulation reaction was allowed to progress for 10-30 minutes, after which point 2-3 gallons of saturated sodium sulfate brine was added to the reaction vessel and agitated for 2 minutes. The mixture was allowed to settle for 10-20 minutes, after which point the aqueous phase was drained and the fatty phase was collected. Table 3 summarizes the results of the acidulation reactions as determined by characteristics of the aqueous phases removed after each reaction.

TABLE 2

| Fatty acid profile of sample | | |
|---|---|---|
| C16 | C18 | C20 |
| 18.7% | 81.0% | 0.3% |

Following the sixth acidulation reaction, the fatty phase comprised 3% unreacted soaps. Therefore, 0.5 kg sodium bisulfate was added to the fatty chase to reduce the unreacted soap content to 0%.

Example 3

Electrolysis of Lipid Phase from Acidulation Reaction

Materials: Two one liter working solutions in 2 L glass beakers with stirbars on 1000 W hotplates being recirculated by constant flow rate peristaltic pumps @60° C. (anolyte is saturated aqueous sodium sulfate and catholyte is 10 wt % sodium hydroxide); 5 cm2 Nafion 115 membrane, PVC body and tubing, 6"×1" DSA, 6"×1" Monel 400 cathode.

Using 0-30 V 0-20 A DC power supply, turn power supply on to provide constant amperage of 3 A to electrodes in PVC system. Pump anolyte and catholyte around with their respective peristaltic pumps at 750 mL/min and heat both to 60° C. Reduce anolyte (side with Na2S04 solution) pH to about 3 to 3.5 before slowly adding enough saponified soapstock to increase pH of anolyte to 5. Stop addition of saponified soapstock and allow electrochemical cell to reduce anolyte pH back to about 3 to 3.5 before adding more saponified soapstock. Halt cycle once 60 minutes of run time has been reached and perform liq-liq extraction of floating fatty material with nonpolar solvent. Rotovap the solvent from crude fatty phase to obtain anhydrous material for characterization.

Result: 12 g fatty material, 1 wt % soap, 99 wt % FFA via titration.

Total energy usage: 1740 kWhr/metric ton FFA produced.

While the forgoing written description of the invention enables one of ordinary skill to make and use what is considered presently to be the best mode thereof, those of ordinary skill will understand and appreciate the existence of variations, combinations, and equivalents of the specific embodiments, methods, and examples herein. The invention should therefore not be limited by the above described embodiments, methods and examples, but by all embodiments and methods within the scope and spirit of the invention.

The invention claimed is:

1. A method for generating free fatty acids from a mixed lipid feedstock, the method comprising:
   providing the mixed lipid feedstock;
   combining the mixed lipid feedstock with a base to form a mixture;
   allowing the mixture to react in a reaction vessel to form a reacted mixture;
   introducing carbon dioxide into the reacted mixture in the reaction vessel to form a first carbonic acid within the reaction vessel;
   mixing the first carbonic acid and the reacted mixture within the reaction vessel; allowing the first carbonic acid and reacted mixture to settle within the reaction vessel; and
   draining a first aqueous layer from the reaction vessel.

2. The method of claim 1, further comprising:
   (a) filtering the first aqueous layer using a size exclusion filtration system;
   (b) the method of (a), wherein the filtering step further comprises a filter having a membrane having a plurality of pores, said pores allowing soaps and phosphates to pass through said membrane of said filter;
   (c) the method of (a), wherein the filtering step further comprises using a filter having a membrane, said membrane allowing particles having a molecular weight less than a molecular weight of a salt;
   (d) the method of (a), wherein the filtering step further comprises maintaining a pH of the first aqueous layer between about 6 and 11;
   (e) the method of (a), wherein the filtering step further comprises maintaining a pressure of the first aqueous layer between about 50 and 800 psi; or
   (f) the method of (a), wherein the filtering step further comprises maintaining a temperature of the first aqueous layer between about 23 and 100° C.

3. The method of claim 1, further comprising an electrolysis step wherein a lipid phase comprising a small amount of unreacted soaps is transferred to an electrolysis unit wherein the unreacted soaps in the lipid phase are reacted with an anolyte to generate free fatty acids.

4. The method of claim 2, further comprising:
   (a) concentrating the first aqueous layer from each step;
   (b) the method of (a), wherein the concentration step further comprises maintaining a pH of the first aqueous layer between about 6 and 11;
   (c) the method of (a), wherein the concentration step further comprises maintaining a pressure of the first aqueous layer between about 0 and 800 psi; or (d) the method of (a), wherein the concentration step further comprises maintaining a temperature of the first aqueous layer between about 23° C. and 100° C.

5. The method of claim 1 further comprising:
combining generated free fatty acids with an alcohol to form a second mixture; and heating and pressurizing the second mixture to above the critical temperature and pressure of the alcohol, thereby esterifying substantially all of the free fatty acids to generate fatty acid alkyl esters.

6. The method of claim 1, further comprising:
(a) combining generated free fatty acids with an alcohol to form a second mixture; and reacting the second mixture to form a fatty alkyl ester;
(b) the method of (a), further comprising using a catalyst to cause the reaction of the mixed lipid feedstock with the base, and optionally the catalyst is an acid catalyst;
(c) removing generated free fatty acids from neutral lipids; and reacting the neutral lipids to form a fatty alkyl ester;
(d) the method of (c), further comprising using a catalyst to cause the reaction, wherein optionally the catalyst is a base catalyst; or
(e) an electrolysis step wherein a lipid phase comprising a small amount of unreacted soaps is transferred to an electrolysis unit wherein the unreacted soaps in the lipid phase are reacted with an anolyte to generate free fatty acids.

7. The method of claim 1, wherein:
(a) the carbon dioxide is introduced as a gaseous flow of carbon dioxide into the reaction vessel; or
(b) the carbon dioxide is introduced as a gaseous flow of carbon dioxide into water and wherein the water is introduced to the reaction vessel.

8. A method for generating free fatty acids from a mixed lipid feedstock, the method comprising:
providing the mixed lipid feedstock;
combining the mixed lipid feedstock with a base to form a first mixture;
allowing the first mixture to react in a reaction vessel to form a reacted first mixture;
combining the reacted first mixture with an organic or inorganic acid, thereby acidulating soaps in the first mixture to generate free fatty acids;
draining a first aqueous layer from the reaction vessel;
combining the generated free fatty acids with an alcohol to form a second mixture; and
heating and pressurizing the second mixture to above the critical temperature and pressure of the alcohol, thereby esterifying substantially all of the free fatty acids to generate fatty acid alkyl esters.

9. The method of claim 8 further comprising an electrolysis step wherein a lipid phase comprising a small amount of unreacted soaps is transferred to an electrolysis unit wherein the unreacted soaps in the lipid phase are reacted with an anolyte to generate free fatty acids.

10. The method of claim 8, wherein:
(a) the organic acid is carbonic acid; and optionally the carbonic acid is generated by adding carbon dioxide to the saponification product mixture, thereby causing the carbon dioxide to react with the water in the saponification product mixture to form a first carbonic acid; or
(b) the method further comprises:
introducing carbon dioxide into the reacted mixture in the reaction vessel to form a second carbonic acid within the reaction vessel;
mixing the second carbonic acid and the reacted mixture within the reaction vessel; allowing the second carbonic acid and reacted mixture to settle within the reaction vessel; and
draining a second aqueous layer from the reaction vessel.

11. A method for generating free fatty acids from a mixed lipid feedstock, the method comprising:
a) providing the mixed lipid feedstock;
b) combining the mixed lipid feedstock with a base to form a first mixture;
c) allowing the first mixture to react in a reaction vessel to form a reacted mixture;
d) introducing carbon dioxide into the reacted mixture in the reaction vessel to form a first carbonic acid within the reaction vessel;
e) mixing the first carbonic acid and the reacted mixture within the reaction vessel;
f) allowing the first carbonic acid and the reacted mixture to settle within the reaction vessel;
g) draining a first aqueous layer from the reaction vessel;
h) removing a generated lipid layer from the reaction vessel; and
i) repeating steps a) through h) above up to 8 times using the generated lipid layer from the reaction vessel as the mixed lipid feedstock for step a).

12. The method of claim 11 further comprising:
(a) adding a salt to the generated lipid layer prior to any of the reactions, wherein optionally the salt is sodium chloride;
(b) adding sodium bisulfate to the generated lipid layer produced in any of the one or more reactions; or
(c) concentrating the first aqueous layer to generate a sodium bicarbonate product that is substantially free of any water, wherein optionally the concentration step further comprises using evaporation, fluidized bed drying, rotary drum drying, lyophilization, spray drying and reverse osmosis.

* * * * *